United States Patent [19]

Givas et al.

[11] 3,988,431

[45] Oct. 26, 1976

[54] RADIOASSAY OF FOLATES

[75] Inventors: Joan K. Givas, Springfield, N.J.; Sidney Gutcho, Monsey, N.Y.

[73] Assignee: Becton, Dickinson and Company, Rutherford, N.J.

[22] Filed: Dec. 12, 1974

[21] Appl. No.: 532,038

[52] U.S. Cl. ............................. 424/1.5; 23/230 B
[51] Int. Cl.² ................. A61K 43/00; G21H 5/02; G01T 1/16
[58] Field of Search ..................... 424/1.5; 23/230 B

[56] References Cited
OTHER PUBLICATIONS

Shaw et al., Chemical Abstracts, vol. 81, No. 13, Sept. 30, 1974, p. 182, Abstract No. 74448w.
Tajuddin et al., Chemical Abstracts, vol. 78, No. 17, Apr. 30, 1973, p. 207, Abstract No. 107854u.
Waxman et al., Chemical Abstracts, vol. 75, No. 16, Oct. 18, 1971, p. 80, Abstract No. 105931f.
DaCosta et al., Chemical Abstracts, vol. 75, No. 19, Nov. 8, 1971, p. 80, Abstract No. 116555n.
Rothenberg et al., Chemical Abstracts, vol. 71, No. 19, Nov. 10, 1969, p. 204, Abstract No. 89684n.

*Primary Examiner*—Benjamin R. Padgett
*Assistant Examiner*—Christine M. Nucker
*Attorney, Agent, or Firm*—Marn & Jangarathis

[57] ABSTRACT

In the radioassay of folates, the standard is prepared by using folic acid (pteroyl glutamic acid; PGA) as the standard folate at a pH of 9.2 to 9.4. At such pH values, folic acid and 5-methyltetrahydrofolic acid (the predominant folate in human serum) have essentially identical reactivity towards folate binders, whereby folic acid can replace unstable 5-methyltetrahydrofolic acid standard for such assays.

8 Claims, No Drawings

RADIOASSAY OF FOLATES

This invention relates to the radioassay of endogenous folate.

Currently endogenous folate is measured by a competitive protein binding technique. In brief, competitive protein binding (CPB) for the assay of folate involves the ability of unlabeled folate in serum or other media to compete with labeled folic acid for a specific folate binder, present in usable concentrates, in such sources as cow's milk, hog kidney, etc., and thereby inhibit the binding of labeled folic acid. As a result of the competitive inhibition, the ratio of bound labeled folic acid to free labeled folic acid diminishes as the concentration of unlabeled folate is increased. Accordingly, the concentration of folate in an unknown sample, e.g., a patient's blood, is obtained by comparing the inhibition observed with that produced by known amounts of folate, as presented in a standard curve.

It is known that the predominant form of folate found in human serum is the reduced 5-methyl derivative of folic acid, 5-methyltetrahydrofolic acid (MTFA) and, accordingly, in preparing the standard to measure endogenous folate, MTFA is employed as the standard folate in combination with labeled folic acid.

It has been found that purified MTFA is very unstable in solution and solutions thereof deteriorate very rapidly, which has presented both production and user problems for folate assay kits.

It has also been found that under conditions in which labeled folic acid and standard MTFA compete simultaneously for binding sites, the sensitivity of the assay is decreased. In an effort to increase sensitivity, an assay was developed in which the standard is prepared, and actual assay effected, in a manner such that standard MTFA or serum sample containing folate is first incubated with the folate binder and labeled folic acid added in a subsequent step to react with remaining binding sites. Although this technique increases sensitivity, the precision of the assay is diminished. In addition, such a technique requires two separate incubation periods which increases the time and difficulty of the assay.

Accordingly, there is a need for an improvement in the technique and kits for effecting radioassay of folate.

An object of the present invention is to provide for improved radioassay of folate.

A further object of the present invention is to provide an improved kit for the radioassay of folate.

These and other objects of the present invention should be apparent from reading the following detailed description thereof.

In accordance with the present invention, there is provided an improved radioassay for folate by using folic acid as the standard folate. More particularly, the standard curve for the radioassay of folate is prepared by incubating folic acid, as the standard folate, labeled folate, preferably radiolabeled folic acid, and folate binder, at a pH of from 9.2 to 9.4. It has been found that at a pH of from 9.2 to 9.4 folic acid and MTFA have an identical reactivity towards folate binders, whereby the major form of endogenous folate in a sample, MTFA, can be measured from a standard prepared using the stable folic acid, as the standard folate for the radioassay. At pH values outside of 9.2 to 9.4, the reactivities of folic acid and MTFA with respect to folate binders are not sufficiently identical to permit accurate measurement of the MTFA concentration in a sample, based on a standard prepared using folic acid as the standard folate.

The folate binder used in the assay may be any one of the wide variety of folate binders, and as representative examples of such binders, there may be mentioned: milk binder, hog kidney binder, pig serum binder, etc. It has been found that at a pH of from 9.2 to 9.4 MTFA and folic acid have identical reactivity towards folate binders (crude or purified) including modified forms of and active parts of such binders, whether present in the reaction in free form or on a solid support.

The tracer or radioactive substance can be any radioactive form of folic acid or folic acid derivative, such as histidine, tyrosine and tyramine derivatives, reactive with the biological binder. The radioactive labeling substance is preferably tritum or one of the radioactive iodines.

The standard is prepared by the general type of procedure known in the art wherein standard samples are prepared having various concentrations of the folic acid standard. The standards and patient samples are diluted by a buffer, followed by heating (15 minutes, in a 100° C bath) where required, to release folates from endogenous serum binders; however, with most serums heating is not required. After cooling to room temperature, a fixed amount of tracer, preferably radiolabeled folic acid, and a fixed amount of folate binder is added to each standard and patient sample, and the mixture is incubated at a pH of from 9.2 to 9.4, maintained by a suitable buffer. The incubation is effected at temperatures known in the art, i.e., temperatures in the order of 4° to 37° C. After incubation, the separation of bound and free folate may be easily achieved by the addition of an adsorbent for the free molecules, such as charcoal, dextran or albumin, coated charcoal, etc. The amount of bound labeled folate in each sample is determined by counting the radioactivity of each sample. The relationship between standard folate concentration and the bound labeled folate, which is preferably expressed as a percent of the trace binding, is plotted. The standard curve is then employed to determine the unknown concentration of folate, in the patient sample, as known in the art. It is to be understood that the bound labeled folate could be expressed, as known in the art, other than by percent of the trace binding; e.g., ratio of bound to free; etc.; however, the most accurate expression is the percent of trace binding. It is also to be understood, as known in the art, that it is possible to determine the amount of free labeled folate in each sample, and use such amounts in preparing the standard curve.

In accordance with the present invention, there can be provided a kit for the assay of folate which includes radiolabeled folate, and folic acid (PGA), as standard folate. The kit may further include a buffer for maintaining a pH of from 9.2 to 9.4. The kit can also include other materials useful in the assay, such as an adsorbent, to be used for separating bound and free folate.

The invention will be described with respect to the following examples, but the scope of the invention is not to be limited thereby.

The following is an illustrative protocol for the radioassay of folate using folic acid as standard folate.

EXAMPLE

Preparation of Folic Acid (PGA) Standard

Folic Acid (2-2.85 mg) is dissolved in 25 ml 0.1M phosphate buffer, pH 7.0. The concentration is determined spectrophotometrically at 282 nm. ($\epsilon^M 282_{nm}$=26,000). An appropriate dilution is made with 0.05M lysine buffer, containing 0.1% gelatin, 0.1% sodium azide and 0.2% sodium ascorbate, pH 9.3 ± 0.1, to give a folic acid concentration of 100 ng/ml. Aliquots of this are further diluted with lysine-gelatin buffer to give five solutions whose concentrations are 1, 2, 5, 10 and 20 ng Folic Acid/ml. (Levels A–E). The standard solutions may then be lyophilized or stored at −20° or 4° C.

Procedure for Folate Radioassay (Using 3H-PGA as Tracer)

A. Standard Curve

1. Polypropylene (or glass) tubes are numbered sequentially from 1 – 16.
2. Lysine-gelatin buffer is added as follows:

| Tubes | Buffer |
| --- | --- |
| 1,2 | 1.4 ml |
| 3,4 | 1.0 ml |
| 5,6 | 900 μl |
| 7–16 | 800 =l |

3. Add Folic Acid Standards (A–E) as follows:

| Tube No. | Folic Acid Standard | Folic Acid as ng/ml |
| --- | --- | --- |
| 5,6 | None | 0 |
| 7,8 | 50 μl A | 1 |
| 9,10 | 50 μl B | 2 |
| 11,12 | 50 μl C | 5 |
| 13,14 | 50 μl D | 10 |
| 15,16 | 50 μl E | 20 |

Mix gently.

4. Tubes (3 and following) are heated at 100° C for 15 minutes. They are then brought back to room temperature.
5. Add 100 μl Folate tracer to all tubes including 1 and 2. Mix well.
6. Add 100 μl Folate binder to all tubes except 1 – 4. Mix well.
7. Incubate the mixture at room temperature for 30 minutes with the exclusion of light.
8. To tubes 3 and following, add 0.4 ml cold dextran coated charcoal suspension (1.87% charcoal suspended in 0.187% dextran solution). Mix well. Allow tubes to stand at room temperature for 5 minutes.
9. Centifuge tubes 3 and following at 1240 x g for 15 minutes in the cold.
10. Decant the supernatants including tubes 1 and 2 into similarly numbered scintillation vials containing 10 ml scintillation fluid. Mix well.
11. Count the radioactivity in the vials for 2 or more minutes with a liquid scintillation counter.

B. Patient's Samples

1. Consecutively number 2 tubes for each patient's sample beginning with 17.
2. Add 800 μl Lysine-gelatin buffer to each tube.
3. Add 50 μl of patient's plasma or serum.
4. From here on steps 4 – 12 in section A are followed for each patient's sample simultaneously with the tubes prepared in section A.

C. Calculations

1. Average the counts found in vials 3 and 4, the "Blank" vials. Subtract the blank from all other tube counts to obtain the corrected counts. Use only the corrected counts in the calculations. Note: The unit of time must be constant for all tubes counted.
2. Average the corrected counts for vials 1 and 2 to give the "Total Count" per assay.
3. Divide the average of the corrected counts for vials 5 and 6 by the corrected Total Count to give the Trace Binding, $B_0$.

$$B_o = \text{Trace Binding} = \frac{\text{average corrected counts for vials 5 and 6}}{\text{corrected Total Count}} \times 100$$

4. Divide the corrected counts for each vial by the average corrected counts for vials 5 and 6 to give the % of Trace Binding for each tube.

$$\% \text{ of Trace Binding} = \frac{\text{corrected counts}}{\text{average corrected counts for vials 5 and 6}} \times 100$$

5. A Standard Curve may be plotted as follows:

Using logit-log paper, plot % of Trace Binding as the ordinate versus ng/ml of Folic Acid Standard on the log scale.

6. The concentration of folate in a patient's sample is obtained by comparison with the Standard Curve. The concentration of Folic Acid Standard that gives the same % of Trace Binding as a patient's serum or plasma is the concentration of folate per ml of specimen.

The present invention is particularly advantageous in that by using folic acid, as the standard folate, there is provided a single phase, competitive assay system with increased sensitivity and good reproducibility. The assay is sufficiently sensitive to permit use of only 50 ul of patient's plasma or serum, and only 2.5 ul of whole blood.

In addition, the assay is specific for folic acid, MTFA and other closely related endogenous folates and is not affected by folate antagonists or antibiotics.

Furthermore, the use of folic acid, as standard folate, increases the life of a kit and assures users of continued accuracy as well as precision over the life of the kit.

Numerous modifications and variations of the present invention are possible in light of the above teachings and, therefore, within the scope of the appended claims, the invention may be practiced otherwise than as particularly described.

What is claimed is:

1. In a process for preparing a standard for the radioassay of folate by incubation of radiolabeled folate, standard folate and folate binder, the improvement comprising:

employing folic acid as the standard and effecting the incubation at a pH of from 9.2 to 9.4.

2. The process of claim 1 wherein the radiolabeled folate is radiolabeled folic acid.

3. The process of claim 2 wherein the radiolabeled folic acid is tritiated folic acid.

4. The process of claim 2 wherein the radiolabeled folic acid is radioiodinated folic acid.

5. In a process for the radioassay of folate, the improvement comprising:
  incubating a plurality of standard samples, each sample containing a fixed concentration of folate binder, a fixed concentration of radiolabeled folate and a different known concentration of folic acid as a standard folate, said incubating being effected at a pH of from 9.2 to 9.4;
  preparing a standard curve from said standard samples;
  incubating a serum sample containing an unknown concentration of folate, said fixed concentration of folate binder and said fixed concentration of said radiolabeled folate incubation being effected at a pH of from 9.2 to 9.4; and
  determining the amount of folate in said serum sample from said standard curve.

6. The process of claim 5 wherein the radiolabeled folate is radiolabeled folic acid.

7. The process of claim 6 wherein the radiolabeled folic acid is tritiated folic acid.

8. The process of claim 5 wherein the radiolabeled folic acid is radioiodinated folic acid.

* * * * *

Disclaimer and Dedication

3,988,431.—*Joan K. Givas*, Springfield, N.J., and *Sidney Gutcho*, Monsey, N.Y. RADIOASSAY OF FOLATES. Patent dated Oct. 26, 1976. Disclaimer and Dedication filed Feb. 20, 1980, by the assignee, *Becton, Dickinson and Company*.

Hereby disclaims and dedicates to te Public the entire remaining term of said patent.

[*Official Gazette, April 29, 1980.*]